US012685434B2

(12) United States Patent　　　　　(10) Patent No.:　US 12,685,434 B2
　　　Ebersole et al.　　　　　　　　　　(45) Date of Patent:　　　Jul. 21, 2026

(54) ENDOSCOPE CLEANING DEVICES

(71) Applicant: Covidien LP, Mansfield, MA (US)

(72) Inventors: Garrett P. Ebersole, Hamden, CT (US); Hari Naga Mahesh Kalepu, North Haven, CT (US); Shirisha Alampally, Hyderabad (IN); Juan A. Gomez, North Haven, CT (US); Ryan S. Pane, Shelton, CT (US); David T. Thompson, Durham, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/720,288

(22) PCT Filed: Oct. 31, 2022

(86) PCT No.: PCT/IB2022/060463

§ 371 (c)(1),
(2) Date: Jun. 14, 2024

(87) PCT Pub. No.: WO2023/111709

PCT Pub. Date: Jun. 22, 2023

(65) Prior Publication Data

US 2025/0057405 A1　　Feb. 20, 2025

Related U.S. Application Data

(60) Provisional application No. 63/289,722, filed on Dec. 15, 2021.

(51) Int. Cl.
*A61B 1/12*　　　　　(2006.01)

(52) U.S. Cl.
CPC .................................... *A61B 1/121* (2013.01)

(58) Field of Classification Search
CPC ...................................................... A61B 1/121
See application file for complete search history.

(56) References Cited

U.S. PATENT DOCUMENTS

| | | |
|---|---|---|
| 4,966,199 A | 10/1990 | Ruschke |
| 8,267,896 B2 | 9/2012 | Hartoumbekis et al. |
| 8,690,764 B2 | 4/2014 | Clark et al. |
| 9,700,378 B2 | 7/2017 | Mowlai-Ashtiani |
| 9,763,567 B2 | 9/2017 | O'Prey et al. |
| 11,412,921 B2 | 8/2022 | Holsten |
| 11,850,106 B2 | 12/2023 | Baril et al. |
| 2002/0022762 A1 | 2/2002 | Beane et al. |

(Continued)

FOREIGN PATENT DOCUMENTS

| | | |
|---|---|---|
| AU | 2007219275 A1 | 4/2008 |
| CN | 107647905 A | 2/2018 |

(Continued)

*Primary Examiner* — Jason Y Ko

(74) *Attorney, Agent, or Firm* — Dymera IP, LLC

(57)　　　　　　　ABSTRACT

An endoscope cleaning device includes a canister, a battery pack, a heating mechanism thermally coupled to the canister, and a pull tab. The canister has defogging solution stored therein for cleaning an endoscope upon insertion of the endoscope into the canister. A cover is secured to the opened upper end of the canister and defines a central opening configured for passage of the endoscope. The pull tab covers the central opening of the cover and is coupled to the battery pack. The pull tab is configured to inhibit electrical communication between a battery and the heating mechanism until the pull tab is detached from the battery pack.

20 Claims, 6 Drawing Sheets

(56)          References Cited

U.S. PATENT DOCUMENTS

| | | |
|---|---|---|
| 2009/0005799 A1 | 1/2009 | Franer et al. |
| 2010/0204546 A1 | 8/2010 | Hassidov et al. |
| 2015/0080660 A1 | 3/2015 | Gomez et al. |
| 2016/0135673 A1 | 5/2016 | Miller et al. |
| 2019/0159665 A1 | 5/2019 | Jadhav et al. |
| 2019/0231183 A1 | 8/2019 | Ahmed et al. |
| 2022/0386859 A1 | 12/2022 | Holsten |
| 2023/0011681 A1 | 1/2023 | Vadali |
| 2023/0165452 A1 | 6/2023 | Ding et al. |
| 2023/0172632 A1 | 6/2023 | Ding et al. |
| 2023/0263382 A1 | 8/2023 | Ding et al. |
| 2024/0115349 A1 | 4/2024 | Baril et al. |

FOREIGN PATENT DOCUMENTS

| | | | |
|---|---|---|---|
| JP | 2000111809 A | 4/2000 |
| JP | 2008291951 A | 12/2008 |
| WO | 2016115310 A2 | 7/2016 |

ENDOSCOPE CLEANING DEVICES

CROSS-REFERENCE TO RELATED APPLICATIONS

This application is a national stage entry of International Application Serial No. PCT/IB2022/060463, filed Oct. 31, 2022, which claims priority to U.S. Provisional Application Ser. No. 63/289,722, filed Dec. 15, 2021. The entire disclosures of which are incorporated herein by reference in their entirety.

FIELD

The disclosure relates to a device for cleaning a lens of an endoscope during a minimally invasive surgical procedure.

BACKGROUND

Minimally invasive surgery eliminates the need to make a large incision in a patient, thereby reducing discomfort, recovery time, and many of the deleterious side effects associated with traditional open surgery. Minimally invasive viewing instruments such as, e.g., laparoscopes and endoscopes, provide viewing of internal tissues and/or organs during the minimally invasive surgery. Laparoscopic surgery involves the placement of a laparoscope in a small incision in the abdominal wall of a patient, to view the surgical site. Endoscopic surgery involves the placement of an endoscope in a naturally occurring orifice, e.g., mouth, nose, anus, urethra, or vagina, to view the surgical site. Other minimally invasive surgical procedures include video assisted thoracic surgery and cardiovascular surgery conducted through small incisions between the ribs. These procedures also utilize scopes to view the surgical site.

A typical minimally invasive viewing instrument, e.g., a laparoscope or an endoscope, includes a housing, an elongated lens shaft extending from one end of the housing, and a lens that is provided in a distal end of the elongated lens shaft. A camera viewfinder extends from the other end of the housing. A camera is connected to the housing and transmits images sighted through the lens to an external monitor on which the images are displayed. During a surgical procedure, the distal end portion of the elongated lens shaft is extended into the patient, while the proximal end portion of the elongated lens shaft, the housing and the camera viewfinder remain outside the patient. In this manner, the laparoscope/endoscope is positioned and adjusted to view particular anatomical structures in the surgical field on the monitor.

During insertion of an endoscope or a laparoscope into the body and during the surgical procedure, debris, e.g., organic matter and/or moisture, may be deposited on the lens of the scope. The buildup of debris and condensation on the lens impairs visualization of the surgical site, and often necessitates cleaning of the lens. An endoscope cleaning device may be utilized to remove debris on the lens and to inhibit fogging of the lens upon the endoscope entering a surgical site.

SUMMARY

In accordance with the disclosure, an endoscope cleaning device includes a housing, a fluid storage assembly disposed within the housing, a battery pack, a heating mechanism, and a pull tab. The fluid storage assembly includes a canister, a seal assembly supported in the canister, and a cover. The canister has a main body defining a chamber, and a collar fixed to an upper rim of the main body. The chamber of the main body has a defogging solution stored therein and is configured to receive an endoscope. The cover is secured to the collar and defines a central opening configured for passage of the endoscope. The heating mechanism is thermally coupled to the canister. The pull tab covers the central opening of the cover and is coupled to the battery pack. The pull tab is configured to inhibit electrical communication between a battery of the battery pack and the heating mechanism until the pull tab is detached from the battery pack.

In aspects, the main body and the collar may be monolithically formed.

In aspects, the main body and the collar may be fabricated from metal.

In aspects, the main body and the collar may be fabricated from plastic.

In aspects, the main body may be fabricated from metal, and the collar may be fabricated from plastic.

In aspects, the collar may be overmolded to the upper rim of the main body.

In aspects, the cover may be welded to the collar, whereby the defogging solution is hermetically sealed in the canister.

In aspects, the cover may be threadedly coupled to the collar.

In aspects, the collar may include a base portion extending radially outward from the upper rim of the main body, and an annular wall protruding upwardly from the base portion. The seal assembly may be supported on the base portion.

In aspects, the seal assembly may include a one-way valve supported on the base portion, and an open seal interposed between the one-way valve and the cover.

In aspects, the one-way valve and the open seal may be compressed between the base portion of the collar and the cover.

In aspects, the annular wall may define an inner groove, and the cover may include an annular projection received in the inner groove.

In aspects, the cover may have a ring-shaped plate that defines the central opening therein. The annular projection may extend from the plate.

In aspects, the plate of the cover may be devoid of holes other than the central opening.

In aspects, the cover may be fabricated from sheet metal and include a ring-shaped plate that defines the central opening therein, and an annular wall extending downwardly from an outer periphery of the plate. The annular wall may have a lower edge crimped to a neck of the collar to compress the seal assembly between the plate and the lower edge.

In aspects, the valve assembly may include a one-way valve supported on the collar, and an open seal interposed between the one-way valve and the plate of the cover. The open seal may have an upper surface defining an annular recess. The annular recess may have an annular ridge of the plate received therein.

In accordance with another aspect of the disclosure, a surgical kit is provided and includes an endoscope and an endoscope cleaning device. The endoscope has a lens at a distal end portion of the endoscope. The endoscope cleaning device includes a canister, a seal assembly supported in the canister, a cover, a battery pack, a heating mechanism thermally coupled to the canister, and a pull tab. The canister includes a main body defining a chamber, and a collar fixed to an upper rim of the main body. The chamber of the main body has a defogging solution stored therein and is configured to receive the distal end portion of the endoscope. The cover is secured to the collar and defines a central opening configured for passage of the distal portion of the endoscope. The pull tab covers the central opening of the cover and is coupled to the battery pack. The pull tab is configured to inhibit electrical communication between the battery and the heating mechanism until the pull tab is detached from the battery pack.

In aspects, the main body and the collar may be monolithically formed from metal or plastic.

In aspects, the main body may be fabricated from metal, and the collar may be fabricated from plastic. The collar may be overmolded to the upper rim of the main body and the cover may be welded to the collar, whereby the defogging solution is hermetically sealed in the canister.

In aspects, the cover may be fabricated from sheet metal and include a ring-shaped plate that defines the central opening therein, and an annular wall extending downwardly from an outer periphery of the plate. The annular wall may have a lower edge crimped to a neck of the collar to compress the seal assembly between the plate and the lower edge.

BRIEF DESCRIPTION OF THE DRAWINGS

The above and other aspects and features of this disclosure will become more apparent in view of the following detailed description when taken in conjunction with the accompanying drawings wherein like reference numerals identify similar or identical elements.

DETAILED DESCRIPTION

Figure 1:
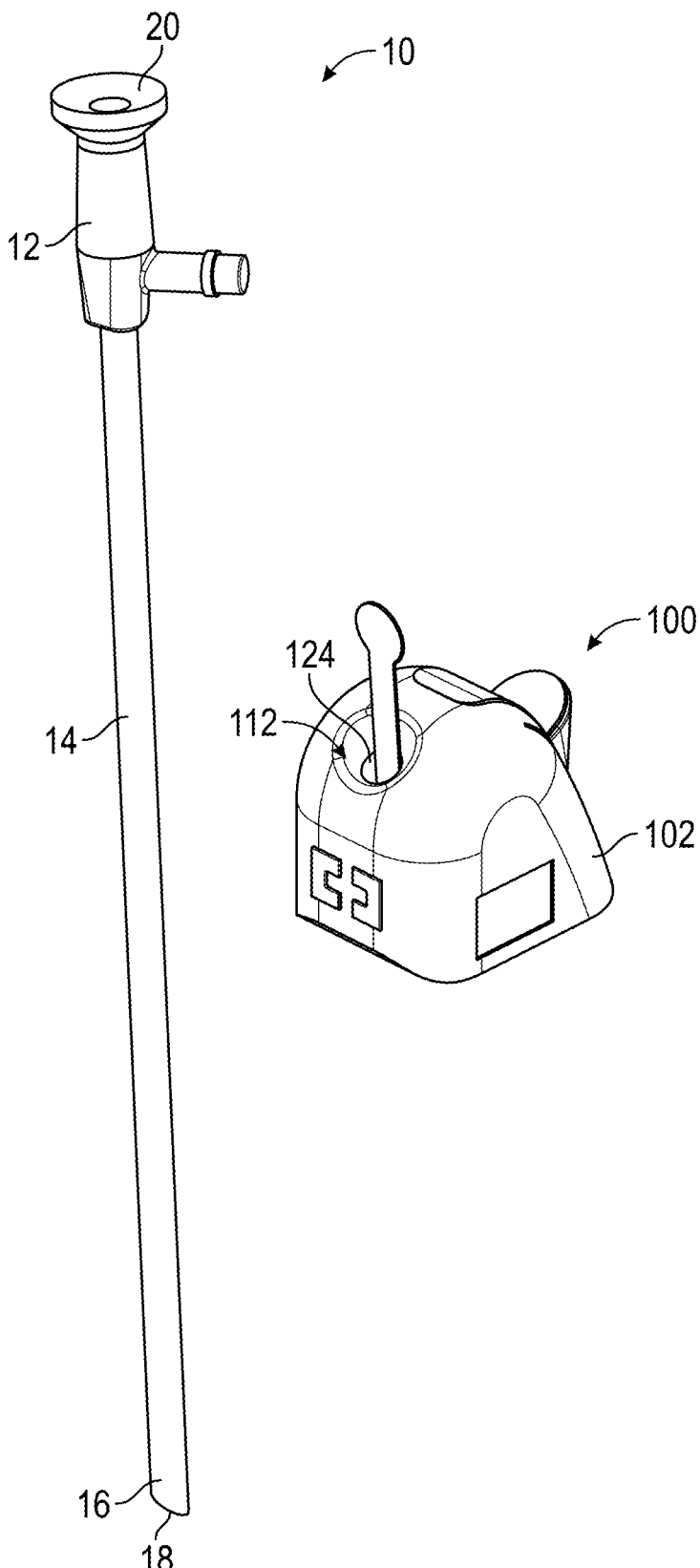
FIG. 1 is a perspective view illustrating a surgical kit including an endoscope and an endoscope cleaning device in accordance with the disclosure.

The endoscope cleaning devices disclosed herein are described in detail with reference to the drawings, in which like reference numerals designate identical or corresponding elements in each of the several views. As used herein, the term "distal" refers to the portion that is being described which is farther from a user, while the term "proximal" refers to the portion that is being described which is closer to a user. Further, to the extent consistent, any or all of the aspects detailed herein may be used in conjunction with any or all of the other aspects detailed herein.

In an endoscope cleaning device, cleaning fluid or defogging solution is sealed within a canister of the endoscope cleaning device prior to use. However, the material of the seal and geometry of a cap on the canister may allow for evaporation of the cleaning fluid over a period of time. As vapor permeates through the seal, the vapor passes through openings in the cap and into the external environment.

This disclosure provides a plurality of ways to prevent and/or inhibit losses of the cleaning fluid via evaporation. In one aspect, the canister may be fabricated from metal and has a plastic rim overmolded to an upper portion of the metal canister. A plastic cap is then welded to the plastic rim. In another aspect, the canister is fabricated entirely from plastic and a plastic cap is welded to the upper portion of the plastic canister. In other aspects, the canister may be metal or plastic and a plastic cap is screwed onto an upper portion of the canister. In further aspects, the canister is made entirely of plastic and a metal cover is crimped onto an upper portion of the plastic canister. Each of these designs creates a hermetic seal between the cap and the canister, is easily and cheaply manufactured, and provides for effective thermal transfer of heat generated by a heating mechanism through the canister and into the cleaning fluid.

Further provided is a heat-sealed pull tab that has the dual function of covering an opening in the cap of the endoscope cleaning device and interrupt a circuit of the endoscope cleaning device until the pull tab is disengaged from a battery of the endoscope cleaning device. The pull tab, in combination with any of the above-noted canister and cap solutions, eliminates evaporation paths for the cleaning fluid within the canister.

With reference to FIG. 1, an endoscope cleaning device in accordance with the disclosure is shown generally as endoscope cleaning device 100. The endoscope cleaning device 100 is configured to receive an endoscope 10 to clean and warm up a lens 18 at a distal end portion 16 of the endoscope 10 prior to and/or during a surgery. The endoscopic cleaning device 100 reduces fogging of the lens 18 of the endoscope 10 and helps to maintain a good field of vision.

FIG. 1 illustrates the endoscope 10 including a housing 12 and an elongated tubular shaft 14 extending distally from the housing 12 and terminating in the lens 18. A distal end portion 16 of the tubular shaft 14 of the endoscope 10 includes a number of optical components that produce images of the patient's tissue as known by one skilled in the art. The optical components generally include a window or front element of a lens assembly that is positioned in front of an image sensor or in front of a fiber optic imaging guide that transfers an image to the proximal end of the endoscope 10. Illumination sources such as, e.g., light-emitting diodes, fiber optic or illumination guides, may also be provided.

The elongate tubular shaft 14 may be rigid, semi-rigid, or flexible. The housing 12 may include a viewfinder 20 adapted to sight images of a surgical field in the patient, e.g., an abdominal cavity, thoracic cavity, etc., as the position of the endoscope 10 is adjusted to view a particular anatomical structure in the surgical field. A camera (not shown) is adapted to receive images of the surgical field sighted through the lens 18 and transmit the images to, e.g., an external monitor (not shown), on which the images of the surgical field are displayed. That is, a visual display device (not shown) converts the optical signal into a video signal to produce a video image on the monitor (or for storage on select media). Accordingly, the monitor enables a clinician to view the anatomical structure in the surgical field inside the patient as the surgical procedure is carried out using minimally invasive or endoscopic surgical instruments.

Fogging of the lens 18 of the endoscope 10 may occur when the lens 18 is introduced into the surgical site. Further, throughout the surgical procedure, condensation, smoke particles, and biological tissue or matter may contact and build up on the lens 18 of the endoscope 10. This tends to obscure the images of the surgical field as they are displayed on the monitor. To this end, the endoscope cleaning device 100 may be utilized during and/or prior to the surgical procedure to maintain a clear image. In particular, the endoscope cleaning device 100 may be utilized to remove debris such as, e.g., organic matter and/or moisture, from the lens 18 of the endoscope 10 and to reduce fogging of the lens 18 upon the endoscope 10 entering a surgical site.

Figure 2:
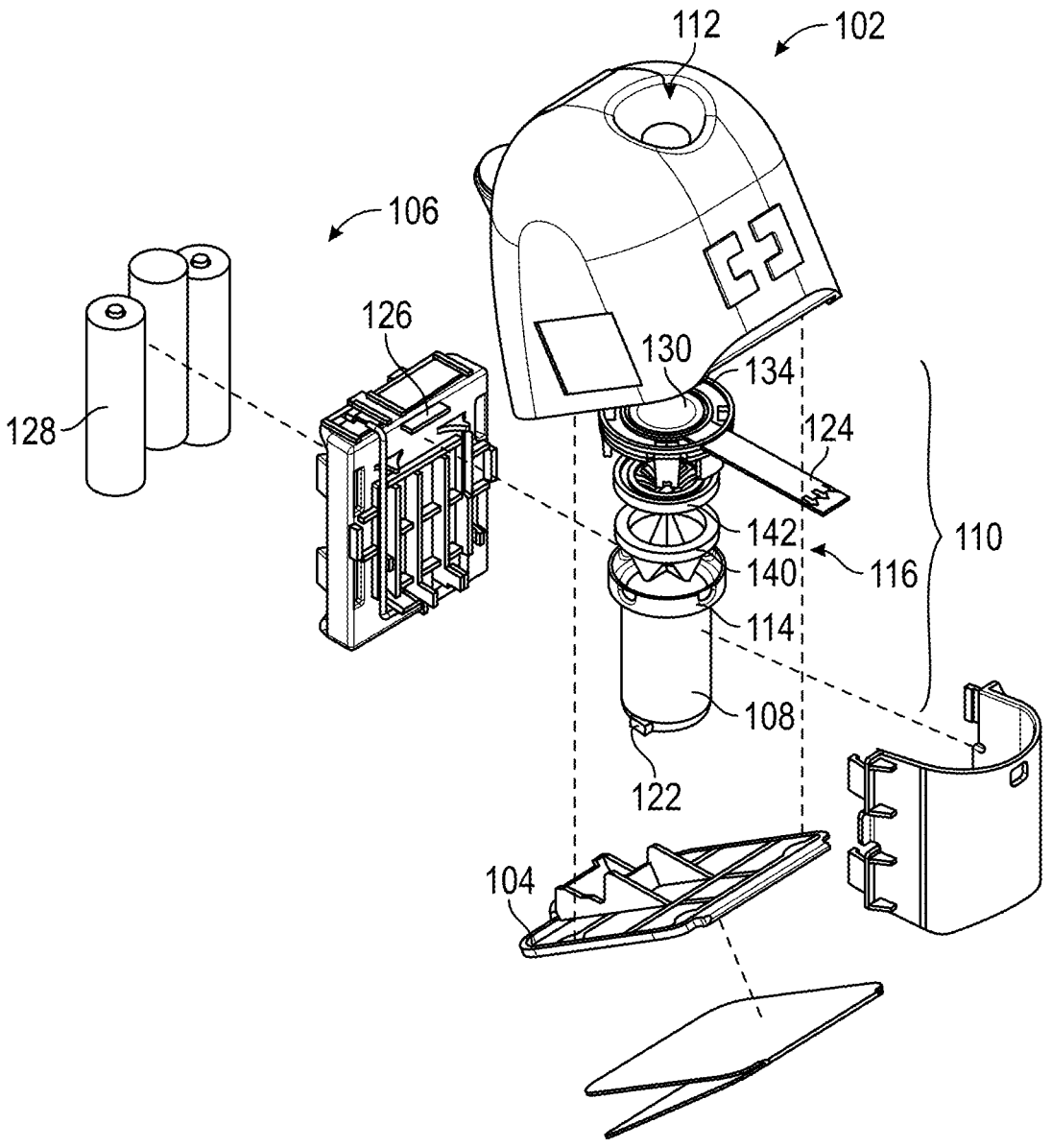
FIG. 2 is a perspective view, with parts separated, illustrating the endoscope cleaning device of FIG. 1.

FIGS. 1 and 2 illustrate the endoscope cleaning device 100 including a housing 102, a base portion 104, a battery pack 106 detachably attached to the base portion 104 and receivable in the housing 102, a heating mechanism 108, and a fluid storage assembly 110. The housing 102 is removably coupled to the base portion 104 and defines an opening 112 configured to receive the shaft 14 of the endoscope 10.

The fluid storage assembly 110 generally includes a canister 114 having stored therein a defogging material (not explicitly shown) and a seal assembly 116, as will be described in further detail below. The defogging material is configured to treat and inhibit the lens 18 of the endoscope 10 from fogging during a surgical procedure. The defogging material may include an antifog, lens cleaning agent, or surfactant solution, in the form of a liquid or gel.

In an aspect, a white balancing reference material or cleaning pad 118 (FIGS. 3 and 4) may be disposed within the canister 114 to balance the color temperature of the image and/or wipe debris from the lens 18. The white balancing reference material 118 may be a true white, soft, non-scratch, absorbent material. For example, the white balancing reference material 118 may include a sponge having a white color with a chromaticity of about D-65 or about a D-50 or about D-100. The white balancing reference material 118 may be made out of a low-density foam or other soft material which can be either hydrophobic or hydrophilic. In an aspect, the white balancing reference material 118 is made out of a white medical grade closed cell foam. In an aspect, the housing 102 may include a microfiber fabric on all or part of an outer surface of the housing 102 so that the lens 18 of the endoscope 10 may be wiped thereon and cleaned during a surgical procedure.

The heating mechanism 108 (FIG. 2) of the endoscope cleaning device 100 is wrapped around the canister 114 of the fluid storage assembly 110 and is in thermal communication with an internal chamber or canal 120 (FIG. 4) defined within the canister 114 for heating the defogging material disposed within the canister 114 to further inhibit the lens 18 of the endoscope 10 from fogging. The heating mechanism 108 may include a heating element such as, e.g., a wound gauge copper wire or nichrome wire, that is connected to the battery pack 106. In an aspect, a thermistor or switch 122 having a thermal component may be placed in an electrical circuit of the heating mechanism 108 to turn off the supply of electricity when a predetermined temperature is reached by the defogging material so as to allow the heating mechanism 108 to maintain a constant temperature of the defogging material above body temperature for an extended period of time while being energized by the battery pack 106.

The fluid storage assembly 110 includes a pull tab 124 interposed between electrical contact portions 126 of the battery pack 106 and batteries 128 of the battery pack 106 to inhibit the batteries 128 from energizing the heating mechanism 108 (FIG. 2). In addition, a seal portion 130 of the pull tab 124 is positioned over an entrance opening 132 (FIG. 3) in a cap or cover 134 of the seal assembly 116 to form a hermetic seal with the seal assembly 116 to thereby contain the defogging material within the canister 114. As such, the pull tab 124 may have the dual function of inhibiting drainage of the batteries 128 and sealing the entrance opening 132 of the seal assembly 116 prior to usage of the endoscope cleaning device 100 (e.g., while the endoscope cleaning device 100 is being shipped and stored).

In use, a grip portion of the pull tab 124 may be pulled by a clinician to remove the pull tab 124 from the battery pack 106 to energize the heating mechanism 108 (FIG. 2) and to detach the seal portion 130 from the seal assembly 116 or otherwise uncover the entrance opening 132 of the seal assembly 116. The heating mechanism 108, in turn, heats the canister 114 and the defogging material disposed therein.

Figure 3:
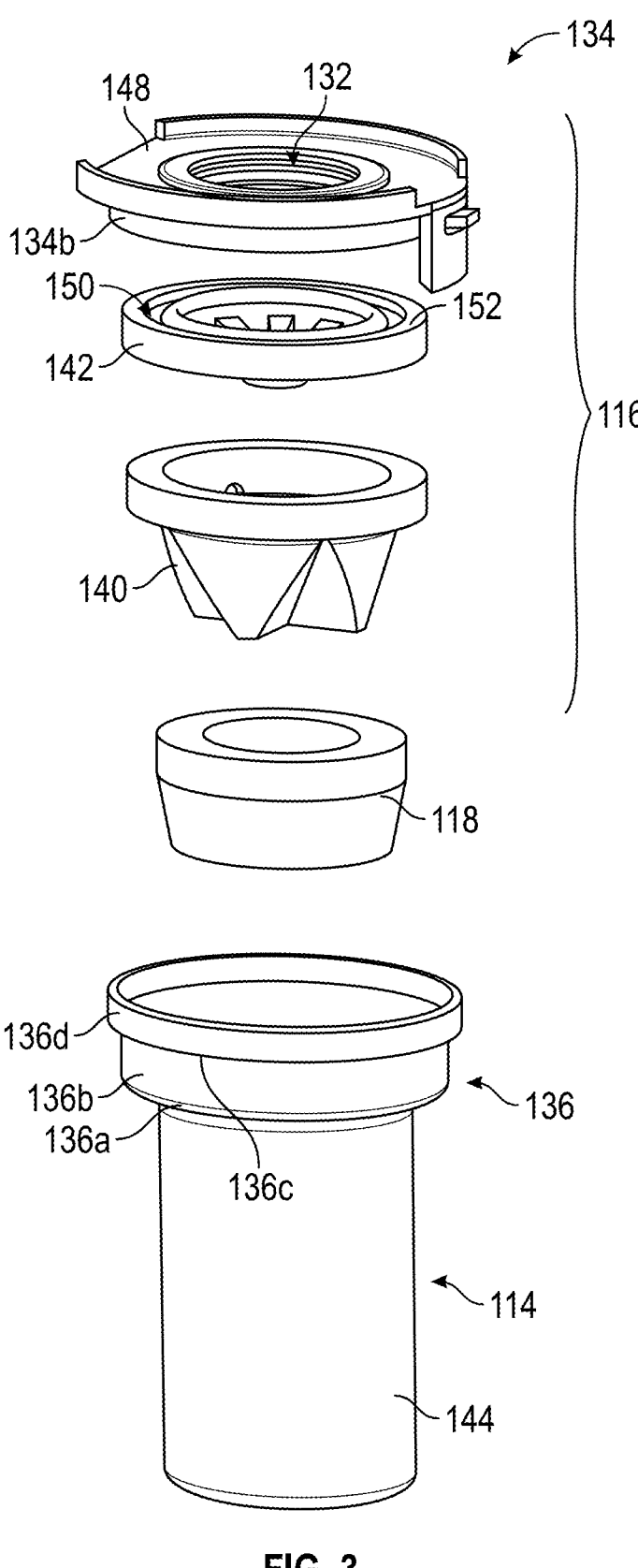
FIG. 3 is a perspective view, with parts separated, illustrating a fluid storage assembly of the endoscope cleaning device of FIG. 1.
Figures 4, 5:
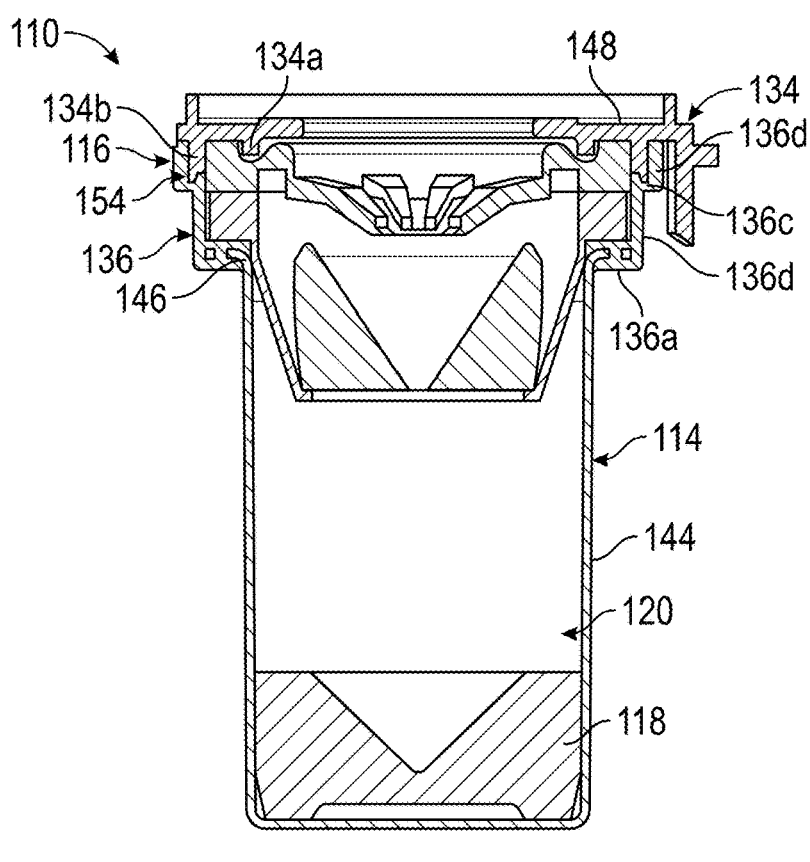
FIG. 4 is a longitudinal cross-sectional view illustrating the fluid storage assembly of FIG. 3.
FIG. 5 is a longitudinal cross-sectional view illustrating another fluid storage assembly of the endoscope cleaning device.

FIGS. 3 and 4 illustrate details of the fluid storage assembly 110. The seal assembly 116 of the fluid storage assembly 110 is disposed at least partly within an upper collar 136 of the canister 114 and is configured to receive the endoscope 10 therethrough and inhibit the defogging material from spilling out of the canal 120 of the canister 114. The seal assembly 116 includes a valve 140, a seal 142, and the cover 134. The valve 140 and seal 142 are disposed within the collar 136 of the canister 114, and the cover 134 is fixed to the collar 136 to seal the valve 140 and seal 142 therein. The valve 140 may be a one-way valve, such as, for example, a duckbill valve, that allows for the insertion of the endoscope 10 therethrough in a distal direction while inhibiting the passage of fluid therethrough in a proximal direction. The seal 142 forms a catch that prevents the defogging material from passing proximally out of a central opening of the seal 142 in the event that the endoscope cleaning device 100 tips over onto its side. The valve 140 and seal 142 may be made of a flexible medical grade silicone plastic. Other suitable materials for the valve 140 and seal 142 are also contemplated.

The canister 114 of the fluid storage assembly 110 includes a main body 144 and the collar 136. The main body 144 is fabricated from metal (e.g., stainless steel) and has a cylindrical shape. Other shapes for the main body 144 are also contemplated. The main body 144 has an upper rim 146 that protrudes radially outward from the main body 144 upon which the collar 136 is overmolded.

The collar 136 of the canister 114 is fabricated from plastic and protrudes upwardly and radially outward from the upper rim 146 of the main body 144. The collar 136 is a monolithic structure having a first base portion 136a overmolded to the upper rim 146, a first annular wall 136b extending upwardly from the first base portion 136a, a second base portion 136c extending radially outward from the first annular wall 136b, and a second annular wall 136d extending upwardly from the second base portion 136c. The first base portion 136a supports the valve 140 and seal 142 thereon, and the second base portion 136c supports and receives an outer annular projection of the cover 134. Overmolding the plastic collar 136 to the upper rim 146 of the canister 114 creates a hermetic seal between the collar 136 and the main body 144.

The cover 134 of the fluid storage assembly 110 is fabricated from plastic and positioned over the seal 142 of the seal assembly 116. The cover 134 is welded to the second base portion 136c and the second annular wall 136d of the collar 136 to compress the valve 140 and seal 142 between the cover 134 and the collar 136. Welding offers controllable compression and eliminates any leak paths for the defogging solution. The cover 134 has an annular plate 148 and inner and outer concentric, annular projections 134a, 134b extending downwardly from the plate 148. The plate 148 of the cover 134 defines the entrance opening 132, which is in vertical registration with a central longitudinal axis of the canister 114. The inner annular projection 134*a* of the cover 134 is received in an annular recess 150 (FIG. 3) defined in an upper surface 152 of the seal 142, and the outer annular projection 134*b* of the cover 134 is received in an annular channel or groove 154 defined between an outer periphery of the seal 142 and an inner periphery of the second annular wall 136*d* of the collar 136. The outer annular projection 134*b* is welded to the second annular wall 136*d* and/or the second base portion 136*c* of the collar 134.

With reference to FIG. 5, another embodiment of a fluid storage assembly 210 of the endoscope cleaning device 100 is provided and is substantially similar to the fluid storage assembly 110 of FIGS. 3 and 4. Only those features that notably distinguish the fluid storage assembly 210 from the fluid storage assembly 110 of FIGS. 3 and 4 will be described in detail.

The fluid storage assembly 210 includes a canister 214 and a cover 234 overmolded to the canister 214. The canister 214 includes a main body 244 and a collar 236 monolithically formed from a plastic. The plastic from which the canister 214 is fabricated may a thermoplastic including, for example, high density polyethylene (HDPE). The cover 234 is fabricated from plastic and welded to the collar 236. The plastic canister 214 effectively transfers heat from the heating mechanism 108 (FIG. 2) to the defogging solution within the canister 214.

Figure 6:
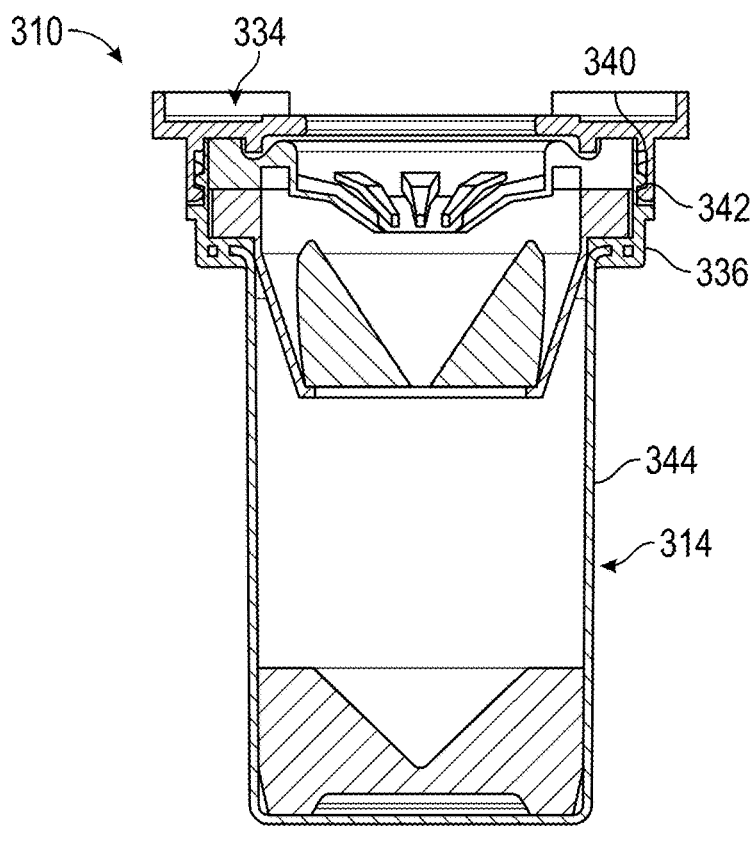
FIG. 6 is a longitudinal cross-sectional view illustrating yet another fluid storage assembly of the endoscope cleaning device.

With reference to FIG. 6, another embodiment of a fluid storage assembly 310 of the endoscope cleaning device 100 is provided and is substantially similar to the fluid storage assembly 110 of FIGS. 3 and 4. Only those features that notably distinguish the fluid storage assembly 310 from the fluid storage assembly 110 of FIGS. 3 and 4 will be described in detail.

The fluid storage assembly 310 includes a canister 314 and a cover 334 threadedly coupled to the canister 314. More specifically, the canister 314 includes a main body 344 and a plastic collar 336 overmolded to the main body 344. It is contemplated that the main body 34 may be fabricated from metal. In other aspects, the main body 344 and collar 336 may be monolithically formed from plastic. The cover 334 is fabricated from plastic and has a threaded inner surface 340 threadedly engaged to a threaded outer surface 342 of the collar 336.

Figure 7:
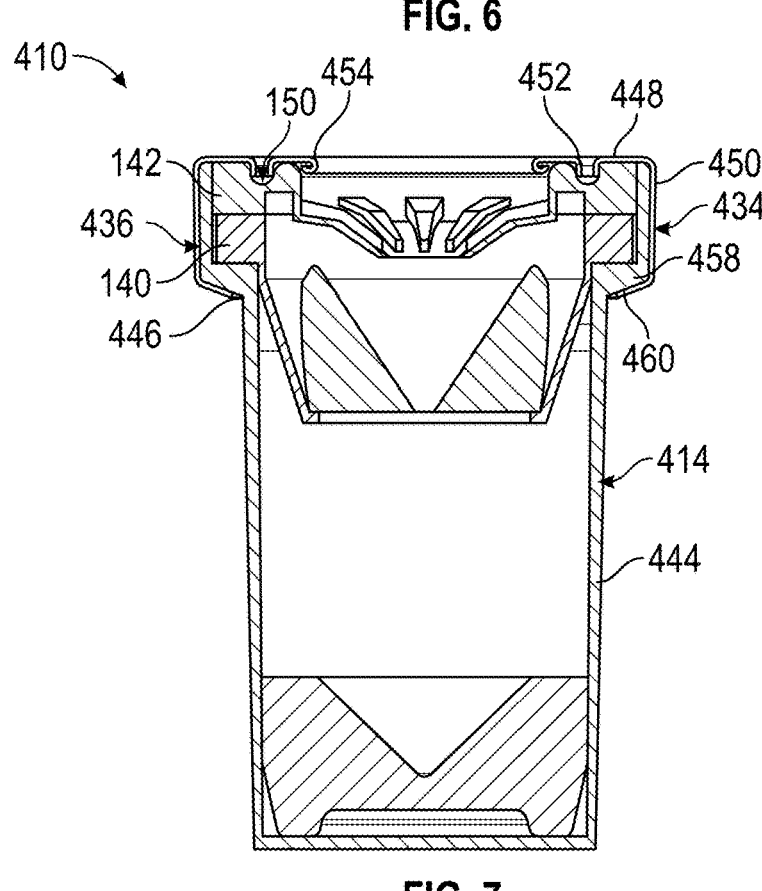
FIG. 7 is a longitudinal cross-sectional view illustrating yet another fluid storage assembly of the endoscope cleaning device.

With reference to FIG. 7, another embodiment of a fluid storage assembly 410 of the endoscope cleaning device 100 is provided and is substantially similar to the fluid storage assembly 110 of FIGS. 3 and 4. Only those features that notably distinguish the fluid storage assembly 410 from the fluid storage assembly 110 of FIGS. 3 and 4 will be described in detail.

The fluid storage assembly 410 includes a canister 414 and a metal cover 434 crimped to the canister 414. More specifically, the canister 414 includes a cylindrical main body 444 and a plastic collar 436 monolithically formed with an upper rim 446 of the main body 444. In aspects, the main body 444 may be fabricated from metal. The cover 434 is fabricated from a piece of sheet metal and has a ring-shaped plate 448 and an annular wall 450 extending downwardly from an outer periphery of the ring-shaped plate 448.

The ring-shaped plate 448 has an annular projection or ridge 452 extending downwardly therefrom, and a curled, circumferential inner edge 454. The ridge 452 extends circumferentially about the plate 448 and has a U-shaped cross-section. The ridge 452 is received in the annular recess 150 of the seal 142 and the curled edge 454 of the plate 448 abuts an inner annular surface of the seal 142. The annular wall 450 of the cover 434 extends around the collar 436 and has a lower end 460 that is crimped around a neck 458 of the collar 436 to secure the cover 434 to the canister 414, whereby the seal 140 and valve 142 are compressed between the ring-shaped plate 448 of the cover 434 and the crimped lower end 460 of the cover 434.

Figure 8:
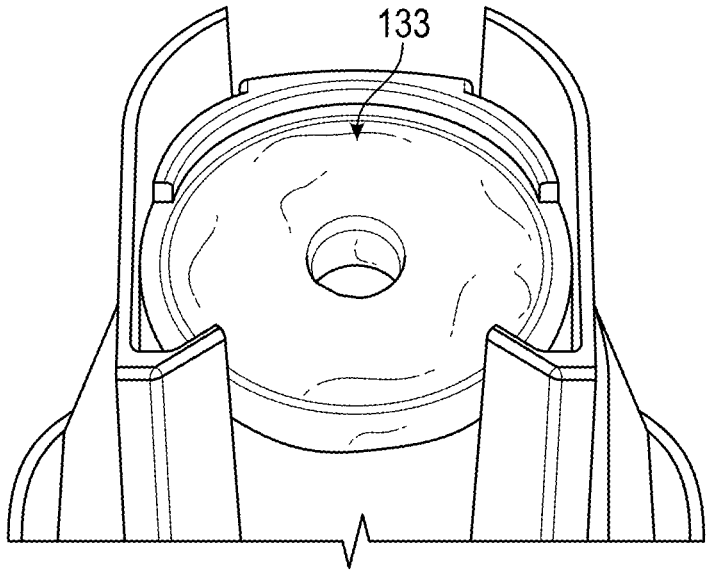
FIG. 8 is a top, perspective view illustrating another fluid storage assembly of the endoscope cleaning device.

With reference to FIG. 8, instead of the pull tab 124 (FIG. 2) covering the entrance opening 132 (FIG. 3) of the cover 134, a puncturable film 133 is provided that is heat staked to the cover 134 to cover the entrance opening 132 thereof.

While the disclosure has been shown in the drawings, it is not intended that the disclosure be limited thereto, as it is intended that the disclosure be as broad in scope as the art will allow and that the specification be read likewise. Therefore, the above description should not be construed as limiting, but merely as exemplifications. Those skilled in the art will envision other modifications within the scope and spirit of the claims appended hereto.

What is claimed is:

1. An endoscope cleaning device comprising:
   a housing;
   a fluid storage assembly disposed within the housing and including:
      a canister including:
         a main body defining a chamber having a defogging solution stored therein and configured to receive an endoscope; and
         a collar fixed to an upper rim of the main body;
      a seal assembly supported within the canister; and
      a cover affixed to the collar to compress the seal assembly within the canister, the cover defining a central opening configured for passage of the endoscope;
   a battery pack having a battery;
   a heating mechanism thermally coupled to the canister; and
   a pull tab covering the central opening of the cover and coupled to the battery pack, wherein the pull tab is configured to inhibit electrical communication between the battery and the heating mechanism until the pull tab is detached from the battery pack.

2. The endoscope cleaning device according to claim 1, wherein the main body and the collar are monolithically formed.

3. The endoscope cleaning device according to claim 2, wherein the main body and the collar are fabricated from metal.

4. The endoscope cleaning device according to claim 2, wherein the main body and the collar are fabricated from plastic.

5. The endoscope cleaning device according to claim 1, wherein the main body is fabricated from metal, and the collar is fabricated from plastic.

6. The endoscope cleaning device according to claim 5, wherein the collar is overmolded to the upper rim of the main body.

7. The endoscope cleaning device according to claim 5, wherein the cover is welded to the collar, whereby the defogging solution is hermetically sealed in the canister.

8. The endoscope cleaning device according to claim 1, wherein the collar includes:
   a base portion extending radially outward from the upper rim of the main body; and
   an annular wall protruding upwardly from the base portion, wherein the seal assembly is supported on the base portion.

9. The endoscope cleaning device according to claim 8, wherein the seal assembly includes:

a one-way valve supported on the base portion; and an open seal interposed between the one-way valve and the cover.

10. The endoscope cleaning device according to claim 9, wherein the one-way valve and the open seal are compressed between the base portion of the collar and the cover.

11. The endoscope cleaning device according to claim 8, wherein the annular wall defines an inner groove, the cover including an annular projection received in the inner groove.

12. The endoscope cleaning device according to claim 11, wherein the cover has a ring-shaped plate that defines the central opening therein, and wherein the annular projection extends from the ring-shaped plate.

13. The endoscope cleaning device according to claim 12, wherein the ring-shaped plate of the cover is devoid of holes other than the central opening.

14. The endoscope cleaning device according to claim 1, wherein the cover is fabricated from sheet metal and includes:

a ring-shaped plate that defines the central opening therein; and an annular wall extending downwardly from an outer periphery of the ring-shaped plate, the annular wall having a lower edge crimped to a neck of the collar to compress the seal assembly between the ring-shaped plate and the lower edge.

15. The endoscope cleaning device according to claim 14, wherein the valve assembly includes:

a one-way valve supported on the collar; and an open seal interposed between the one-way valve and the ring-shaped plate of the cover, the open seal having an upper surface defining an annular recess configured to receive an annular ridge of the ring-shaped plate therein.

16. A surgical kit comprising:

an endoscope having a lens at a distal end portion of the endoscope; and an endoscope cleaning device including:

a canister including:

a main body defining a chamber having a defogging solution stored therein and configured to receive the distal end portion of the endoscope; and a collar fixed to an upper rim of the main body;

a seal assembly supported in the canister;

a cover secured to the collar to compress the seal assembly in the canister, the cover defining a central opening configured for passage of the distal portion of the endoscope;

a battery pack having a battery;

a heating mechanism thermally coupled to the canister; and a pull tab covering the central opening of the cover and coupled to the battery pack, wherein the pull tab is configured to inhibit electrical communication between the battery and the heating mechanism until the pull tab is detached from the battery pack.

17. The surgical kit according to claim 16, wherein the main body and the collar are monolithically formed from metal or plastic.

18. The surgical kit according to claim 16, wherein the main body is fabricated from metal and the collar is fabricated from plastic, and wherein the collar is overmolded to the upper rim of the main body and the cover is welded to the collar, whereby the defogging solution is hermetically sealed in the canister.

19. The surgical kit according to claim 16, wherein the cover is fabricated from sheet metal and includes:

a ring-shaped plate that defines the central opening therein; and an annular wall extending downwardly from an outer periphery of the ring-shaped plate, wherein the annular wall has a lower edge crimped to a neck of the collar to compress the seal assembly between the ring-shaped plate and the lower edge.

20. An endoscope cleaning device comprising:

a housing;

a fluid storage assembly disposed within the housing and including:

a canister including:

a main body defining a chamber having a defogging solution stored therein and configured to receive an endoscope; and a collar fixed to an upper rim of the main body;

a seal assembly supported within the canister, the seal assembly comprising:

a cover secured to the collar and defining a central opening configured for passage of the endoscope;

a one-way valve supported by the collar within the canister; and an open seal interposed between the one-way valve and the cover, wherein the cover when secured to the collar compresses the one-way valve against the open seal;

a battery pack having a battery;

a heating mechanism thermally coupled to the canister; and a pull tab covering the central opening of the cover and coupled to the battery pack, wherein the pull tab is configured to inhibit electrical communication between the battery and the heating mechanism until the pull tab is detached from the battery pack.

* * * * *